US00PP19446P3

(12) United States Plant Patent

Bedford et al.

(10) Patent No.: US PP19,446 P3

(45) Date of Patent: Nov. 11, 2008

(54) APPLE TREE NAMED 'WILDUNG'

(50) Latin Name: *Malus domestica*
Varietal Denomination: Wildung

(75) Inventors: David S. Bedford, New Germany, MN (US); James J. Luby, St. Paul, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 112 days.

(21) Appl. No.: 11/580,545

(22) Filed: Oct. 13, 2006

(65) Prior Publication Data

US 2007/0089207 P1 Apr. 19, 2007

Related U.S. Application Data

(60) Provisional application No. 60/728,237, filed on Oct. 19, 2005.

(51) Int. Cl.
*A01H 5/00* (2006.01)

(52) U.S. Cl. ..... Plt./161

(58) Field of Classification Search ..... Plt./161
See application file for complete search history.

(56) References Cited

U.S. PATENT DOCUMENTS

PP7,197 P * 3/1990 Luby et al. ..... Plt./161
2007/0089207 P1 * 4/2007 Bedford et al. ..... Plt./161

OTHER PUBLICATIONS

University of Minnesota biography of Dr. David K. Wildung available at: http://ncroc.cfans.umn.edu/Dr_David_Wildung.html.*

* cited by examiner

*Primary Examiner*—Wendy C. Haas
(74) *Attorney, Agent, or Firm*—Penny J. Aguirre

(57) ABSTRACT

A new cultivar of Apple tree, 'Wildung', is a late season cultivar that has shown to be hardy and productive for twenty-two years in east central Minnesota. The fruit is characterized by moderately firm, fine-grained flesh, with low acidity and a sweet taste with slight acid balance and rich overtones. The flesh of the fruit is very white and unusually slow to oxidize when exposed to air.

3 Drawing Sheets

Botanical Classification: *Malus domestica*.
Varietal Denomination: 'Wildung'.

BACKGROUND OF THE INVENTION

The present invention relates to a new and distinct cultivar of apple tree, botanically known as *Malus domestica* 'Wildung', referred to hereafter by its cultivar named, 'Wildung'.

'Wildung' is a late season apple cultivar that has been shown to be hardy and productive for 22 years in east Central Minnesota. The fruit of 'Wildung' is characterized by moderately firm, fine-grained flesh with a sweet, rich flavor. The flesh is also notable in its resistance to oxidation when exposed to air.

'Wildung' was discovered in 1983 as a seedling by the inventors as Tree 47 in Row 14 of Block 6 in a trial plot in Ecelsior, Minn. The new apple arose from a cross designated AE 7022 made in 1970 between 'Sharon' (female parent) and 'Connell Red' (male parent). Both parents are unpatented.

Asexual reproduction of the new cultivar was first accomplished by means of budding and grafting by the inventors in Excelsior, Minn. The propagated progeny of 'Wildung' have been determined to be stable and are reproduced true to type in successive generations.

SUMMARY OF THE INVENTION

The following traits have been repeatedly observed and represent the characteristics of the new cultivar. 'Wildung' has not been observed under all possible environmental conditions. The phenotype may vary somewhat with variations in temperature, day length, light intensity, soil types and water and fertility levels, without, however, any variance in the genotype. The measurements, observations and descriptions that follow describe plants grown outdoors and observed for twenty-two years in Excelsior, Minn.

1. 'Wildung' is a late season producer with fruit ripening occurring approximately between October 3rd and October 10th in Excelsior, Minn. Ripening time is similar or slightly later than 'Haralson' (unpatented) and slightly prior to 'Regent' (unpatented) and 'Fireside' (unpatented) and approximately two weeks after 'Honeycrisp' (U.S. Plant Pat. No. 7,197).
2. Fruit size of 'Wildung' ranges from 7.1 to 7.9 cm in diameter with a mean diameter of 7.3 cm. The fruit is smaller than 'Connell Red' and 'Fireside', which are commercial apples ripening at the same time of the season in Minnesota.
3. Fruit color of 'Wildung' is 65 to 85% red, occasionally with bronze-red tones, over yellow-green.
4. The fruit of 'Wildung' is firm to crisp with a fine to intermediate texture and oblate to globose in shape.
5. The flavor of the fruit of 'Wildung' is sweet and rich with low acidity, richer in flavor than 'Connell Red' and 'Fireside'.
6. The storage life of refrigerated 'Wildung' fruit is 60 to 80 days.
7. The flesh of the fruit of 'Wildung' is very white and unusually resistant to oxidative browning.

8. 'Wildung' bears fruit annually and small, unripe fruit have not been commonly observed.
9. 'Wildung' has been shown to be hardy and productive for 22 years in east central Minnesota.

'Wildung' is distinguished from its parent 'Connell Red' in having smaller fruit size ('Wildung' is 7.1 to 7.9 cm in diameter whereas 'Connell Red' is 7.5 to 9.4 cm). The red overcolor of 'Wildung' is often more bronze than the overcolor of 'Connell Red'. The flesh of 'Wildung' exhibits little to no browning when cut or otherwise exposed to air whereas flesh of 'Connell Red' will brown extensively. The fruit of 'Wildung' is slightly more acidic than the fruit of 'Connell Red'.

'Wildung' is distinguished from its parent 'Sharon' in having white flesh color whereas 'Sharon' has cream flesh color. The fruit have a blushed red overcolor in 'Wildung' and striped red overcolor in 'Sharon'.

BRIEF DESCRIPTION OF THE DRAWINGS

The accompanying color photographs were taken in Excelsior, Minn. and illustrate the distinguishing characteristics of the new cultivar 'Wildung'. The colors in the photographs are as close as possible with the photographic and printing technology utilized. The color values cited in the detailed botanical description accurately describe the colors of the new apple tree.

DETAILED BOTANICAL DESCRIPTION

Figure 1:
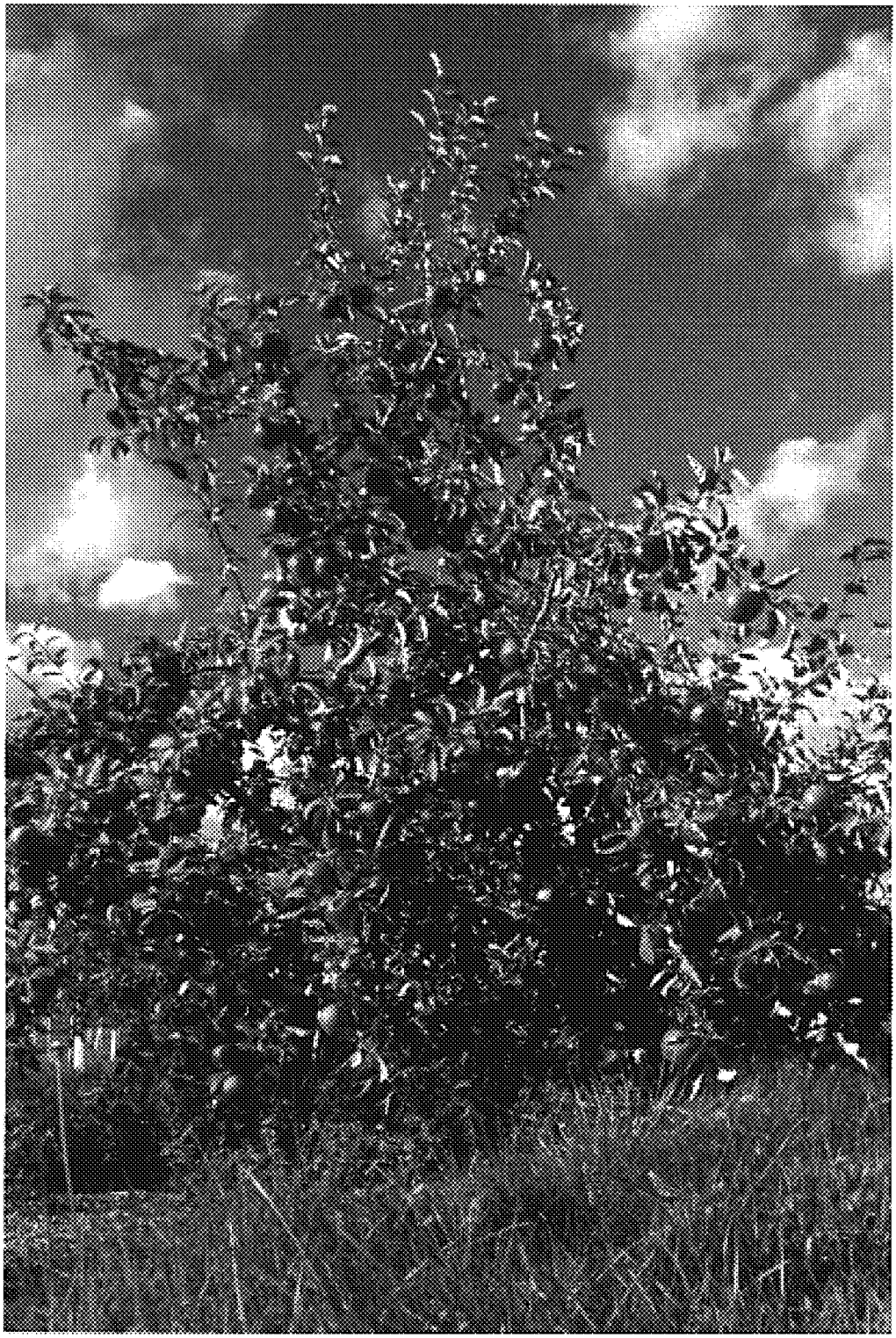
FIG. 1 shows a six year-old tree of 'Wildung'.
Figure 2:
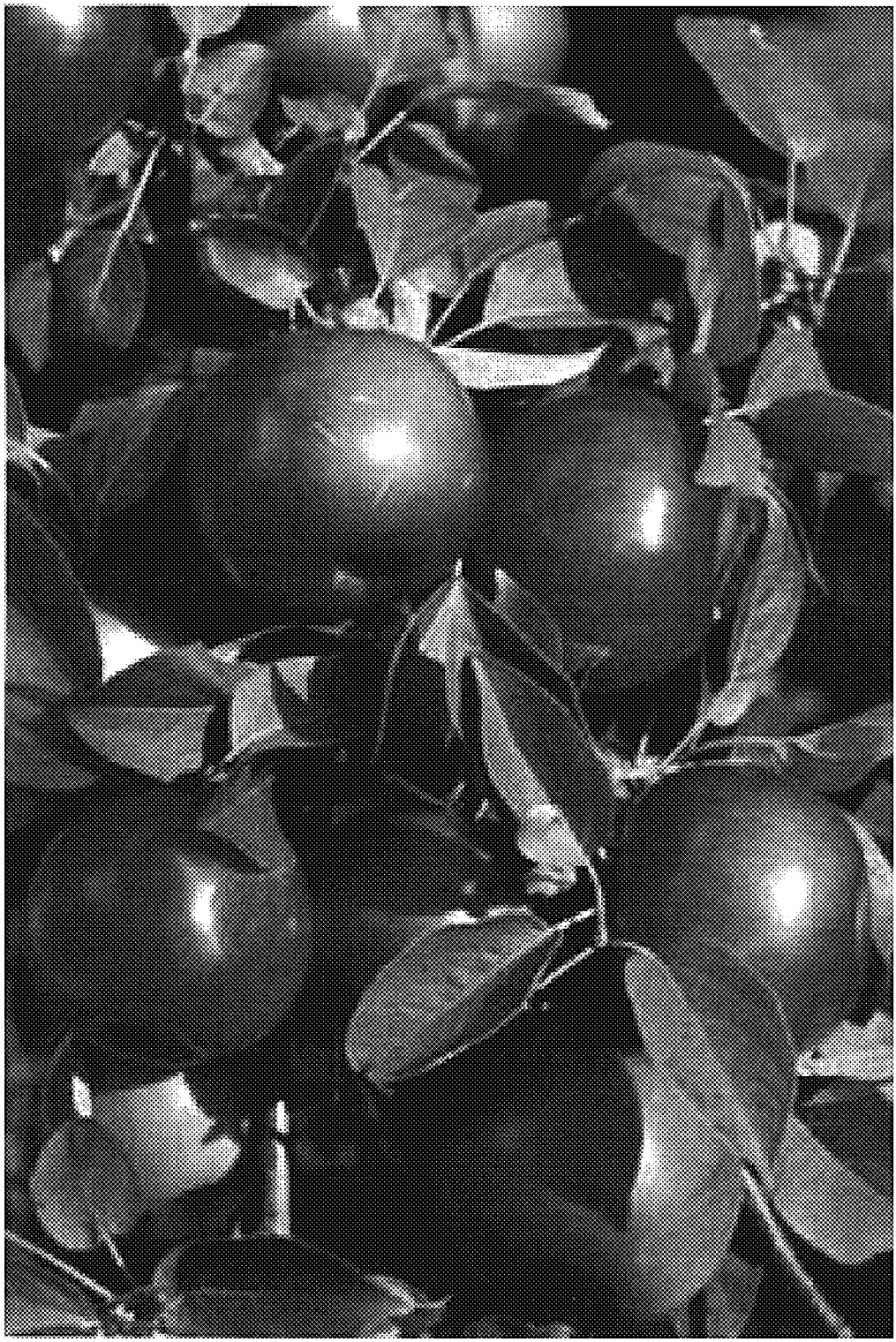
FIG. 2 shows a branch of 'Wildung' with fruit.
Figure 3:
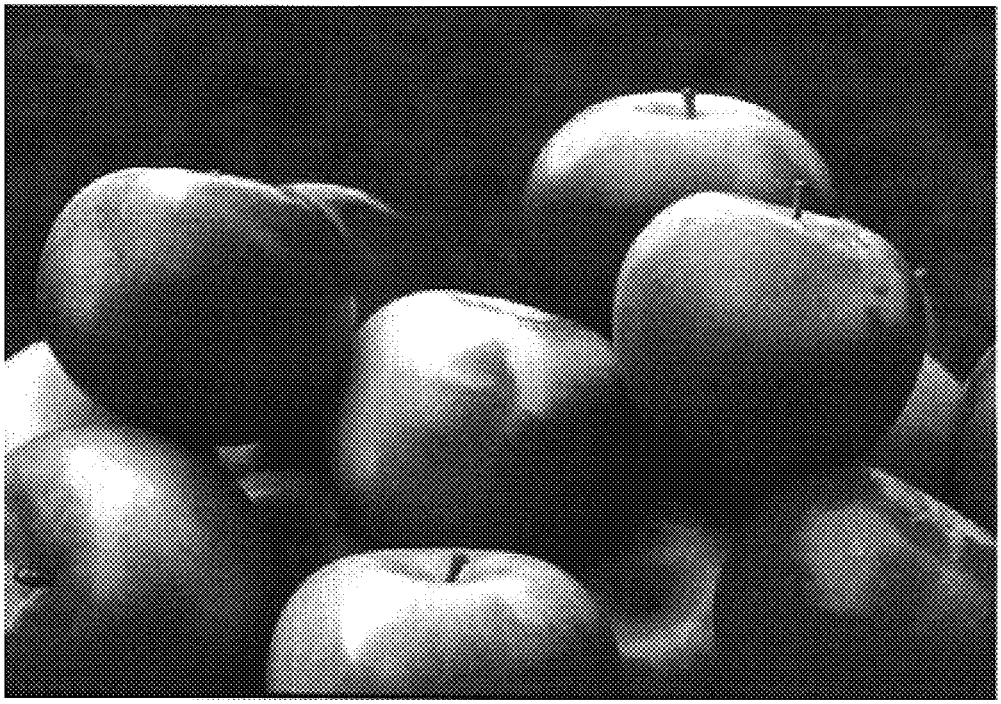
FIG. 3 provides a close-up view of a group of fruit of 'Wildung'.
Figure 4:
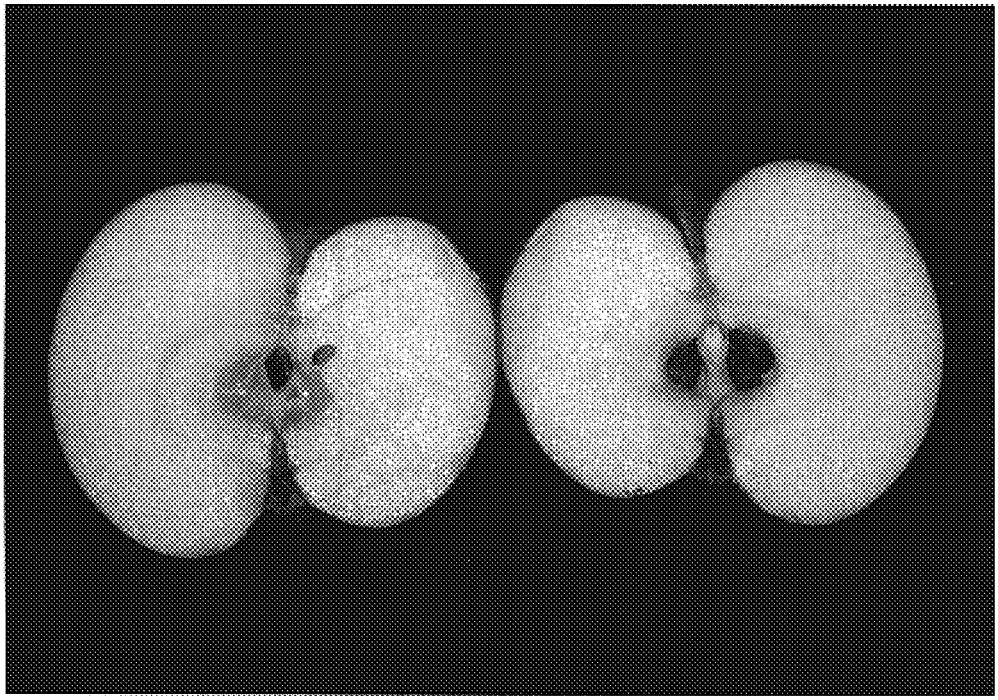
FIG. 4. provides a close-up view of the flesh of a mature fruit of 'Wildung'.

The following is a detailed description of the new apple tree as grown under outdoor field conditions for twenty-two years in Excelsior, Minn. The color names and numbers refer to The 1995 Royal Horticultural Society's Colour Chart, London, England; except for general color terms of ordinary dictionary significance are used.

Botanical classification: Cultivar of *Malus domestica.*
Parentage: 'Connell Red' (female), 'Sharon' (male).
Tree description:
- *Tree habit.*—Somewhat pendant and open.
- *Vigor.*—Moderate.
- *Disease resistance.*—Average to above resistant to apple scab. More resistance than 'Cortland', 'McIntosh' and 'Fireside' (all unpatented) and less resistant than 'Honeycrisp' or 'Freedom' (unpatented). Has shown above average resistance to fire blight in controlled inoculations and field observations.
- *Hardiness.*—U.S.D.A. Zone 4a.
- *Branching habit.*—Spreading to drooping.
- *Branch frequency.*—Medium.
- *Branch strength.*—Intermediate.
- *Angle of bearing branches.*—Approximately 80 to 90°.
- *Predominance of bearing.*—Both spurs and shoots (including tips of shoots).

Description of dormant shoots:
- *Pubescence on upper one year old shoot.*—Variable, generally weak but medium to heavy in some areas.
- *Shine of bark.*—Weak to medium.
- *Thickness of shoot at center middle internode.*—Mean 3.6 mm (range 3.0 to 4.2 mm).
- *Bark color (measured on 1 year-old shoot well exposed to sunlight).*—Dark reddish brown 187A.
- *Lenticel.*—Medium in size and number; color 155C.

Description of growing shoots:
- *Color of growing tip of shoot.*—193C.
- *Shape of shoot tip leaves in cross section.*—Concave.
- *Pubescence.*—Weak to medium on upper side of leaf and dense on lower side.
- *Color of shoot tip leaves.*—Lower side 193C and upper side 144A.
- *Distribution of color other than green on shoot tip leaves.*—Occasionally a small amount of anthocyanin at the apex but most leaves have none.

Leaf description:
- *Leaf orientation.*—Outward.
- *Leaf division.*—Simple.
- *Leaf shape.*—Oval to ovate.
- *Leaf size.*—7.06 cm in length and 4.47 cm in width ($4^{th}$ to $6^{th}$ leaf).
- *Leaf apex.*—Acuminate to cuspidate.
- *Leaf base.*—Rounded to oblique.
- *Leaf surface.*—Medium glossiness on upper surface, pubescent on lower surface.
- *Leaf margin.*—Crenate.
- *Leaf color.*—Upper surface 147A, lower surface 147C.
- *Leaf anthocyanin on lower surface.*—Only at base of petiole 187B.
- *Leaf venation.*—Pinnate major veins with netted minor veins.
- *Petiole size.*—Average of 3.06 cm in length and 1.8 mm in diameter.
- *Petiole color.*—145B.
- *Stipules.*—Small.

Flower description:
- *Flowering date.*—Typically begins between May $5^{th}$ and May $9^{th}$, mid season, before 'Connell Red' and 'Honeycrisp'.
- *Number of flowers.*—5 per cluster.
- *Inflorescence type.*—Corymb of rotate flowers.
- *Flower buds.*—60D in color at pink tip stage, round to conical in shape, average of 9.8 mm in length and 4.9 mm in diameter (at pink tip stage).
- *Flower size.*—Average of 4.8 mm in diameter, 1.4 cm in depth.
- *Flower fragrance.*—Mild.
- *Flower aspect.*—Upright.
- *Petals.*—5 per flower, un-fused, touching to slightly overlapping, ovate in shape, obtuse apex, round base, entire margin, about 2 cm in length and 1.5 cm in width, color of upper surface is almost pure white (155D is closest), color of lower surface is white (closest to 155D) tinged with purple 77C.
- *Sepals.*—5 per flower, 146D in color with tips 78B (upper and lower surface), moderate pubescence, triangular in shape, entire margin, acute apex, fused base, average of 6.4 mm in length and 3.3 mm in width.
- *Pedicel.*—146D in color, average of 1.6 cm in length and 1.9 mm in width.
- *Pistil.*—Compound carpel with 5 stigmas fused at base, 8 mm in length, style is 150B in color and 5 mm in length, stigma is 151A in color, ovary is moderately pubescent and 193A in color.
- *Stamens.*—About 19 per flower, anther is oblong in shape 5D in color and 2 mm in length, pollen is 1C in color and moderate in abundance.

Fruit description:

*Fruit size.*—Mean diameter 7.3 cm (range 7.1to 7.9 cm) in diameter, mean height 5.9 cm (range 5.0 to 6.4 cm).

*Position of maximum diameter.*—Midway between proximal and distal ends.

*Fruit shape.*—Flat globose (oblate) to globose.

*Fruit symmetry.*—Mostly asymmetric.

*Fruit prominence of ribbing.*—Very weak.

*Fruit aperture of eye.*—Usually closed.

*Size of eye.*—Medium, mean 7 mm (range 5 to 10 mm).

*Persistence of calyx.*—Present.

*Length of sepal.*—Medium, mean 3.5 mm (range 2 to 6 mm).

*Spacing of sepals at base.*—Touching to overlapping.

*Depth of eye basin.*—Medium, mean 8 mm (range 6 to 10 mm).

*Width of eye basin.*—Medium, mean 33 mm (range 32 to 37 mm).

*Thickness of stalk.*—Medium, mean 2.4 mm (range 1.7 to 3.5 mm).

*Length of stalk.*—Short to medium, 17 mm (range 10 to 25 mm).

*Depth of stalk cavity.*—Medium, mean 12 mm (range 10 to 17 mm).

*Width of stalk cavity.*—Mean 36 mm (range 10 to 17 mm).

*Relief of surface.*—Smooth.

*Bloom of skin.*—Present.

*Waxiness of skin.*—Medium.

*Thickness of skin.*—Medium.

*Skin color.*—Green-yellow (151A) with 65 to 85% dark red (53A and 46A) to brown red (178C) blushed overcolor, overcolor amount is medium to high and dependent on sun exposure.

*Presence of russet.*—Very low, positioned around stalk cavity.

*Lenticels.*—Small, mean diameter 0.9mm (range 0.2 to 1.7mm), slightly prominent.

*Color of flesh.*—White (whiter than 155B).

*Distinctness of core line.*—Medium.

*Aperture of locules.*—Closed.

*Fruit set.*—Intermediate to good.

*Fruit bearing habit.*—Annually, small unripe fruit have not been commonly observed.

*Fruit maturity date.*—Late season producer with fruit ripening occurring approximately between October 3rd and October 10th in Excelsior, Minn.

*Seed.*—Tan (165B) to dark brown (166A), ovoid to curved deltoid in shape, length 9.2 mm (range 8.0 to 11.0 mm) and maximum diameter 4.5 mm (range 4.0 to 6.0 mm).

*Browning of flesh.*—Absent or weak (resistant to oxidation).

*Fruit flavor.*—Sweet and rich with low acidity.

*Firmness (no skin).*—Firm to crisp, average 15.2 lbs ('Connell Red' 17.4 lbs).

*Texture of flesh.*—Fine to intermediate.

*Juiciness.*—Medium.

*Cropping frequency.*—Annually.

*Acidity.*—0.4585% titratable acidity as malic acid equivalents ('Connell Red' 0.4082% and 'Honeycrisp' 0.5042%).

*Brix.*—13.45° ('Connell Red' 12.6° and 'Honeycrisp' 14.7°)

*Storage life.*—60 to 80 days in common storage (34 to 37° F.) , may be susceptible to soft scald under certain conditions.

We claim:

1. A new and distinct cultivar of apple tree plant named 'Wildung' as herein illustrated and described.

* * * * *